US011535612B2

(12) United States Patent
Delamare et al.

(10) Patent No.: US 11,535,612 B2
(45) Date of Patent: Dec. 27, 2022

(54) AUTONOMOUS DEVICE FOR MEASURING THE CHARACTERISTICS OF A FLUID CIRCULATING IN A CONDUIT AND SYSTEM FOR CONTROLLING VENTILATION, AIR CONDITIONING AND/OR HEATING USING SUCH A DEVICE

(71) Applicant: Enerbee, Grenoble (FR)

(72) Inventors: Jérôme Delamare, Quaix en Chartreuse (FR); Maxime Vincent, Grenoble (FR); Jeremy Laville, Grenoble (FR); Thibault Ricart, Seyssinet Pariset (FR); Luc Pouyadou, Brignoud (FR); Guillaume Maj, Aint-Martin-d'Uriage (FR); Vivien Aumelas, Echirolles (FR); Samuel Guilaume, Grenoble (FR)

(73) Assignee: Enerbee, Grenoble (FR)

( * ) Notice: Subject to any disclaimer, the term of this patent is extended or adjusted under 35 U.S.C. 154(b) by 521 days.

(21) Appl. No.: 16/341,781

(22) PCT Filed: Oct. 12, 2017

(86) PCT No.: PCT/FR2017/052814
§ 371 (c)(1),
(2) Date: Apr. 12, 2019

(87) PCT Pub. No.: WO2018/069656
PCT Pub. Date: Apr. 19, 2018

(65) Prior Publication Data
US 2021/0033296 A1 Feb. 4, 2021

(30) Foreign Application Priority Data
Oct. 12, 2016 (FR) ...................... 1659863

(51) Int. Cl.
*G05D 7/06* (2006.01)
*F17D 3/01* (2006.01)
(Continued)

(52) U.S. Cl.
CPC ............ *C07D 407/04* (2013.01); *A61P 31/00* (2018.01); *C07D 239/47* (2013.01); *C07H 19/06* (2013.01);
(Continued)

(58) Field of Classification Search
CPC . F17D 3/01; F24F 11/63; G01D 21/00; H02K 7/1823; G05B 23/0283;
(Continued)

(56) References Cited

U.S. PATENT DOCUMENTS 4,503,712 A * 3/1985 Vigneaux .................. G01F 1/10
73/861.351
4,887,469 A * 12/1989 Shoptaw ................. G01F 1/065
73/861.77
(Continued)

FOREIGN PATENT DOCUMENTS

| CN | 105683560 A | 6/2016 |
|---|---|---|
| CN | 105762980 A | 7/2016 |

(Continued)

OTHER PUBLICATIONS

Lafont et al., "Magnetostrictive piezoelectric composite structures for energy harvesting," Journal of Micromechanics & Microengineering, vol. 22, No. 9, Aug. 24, 2012, pp. 1-6.
(Continued)

*Primary Examiner* — Jeffrey P Aiello
(74) *Attorney, Agent, or Firm* — TraskBritt

(57) ABSTRACT

An autonomous device for measuring at least one characteristic of a fluid circulating in a conduit in a flow direction comprises a permanent magnetic field source, a magneto-
(Continued)

electric converter and a processing circuit capable of using the electric charges supplied by the converter to supply a measurement of a characteristic of its environment. The source and the converter are placed in a stator and a rotor forming the device. The autonomous device further comprises attachment means allowing the stator to be fixedly placed in the conduit or at one end of the conduit, in a configuration in which the axis of rotation of the rotor is parallel to the flow direction. A control system may employ at least one such autonomous device.

14 Claims, 9 Drawing Sheets

(51) Int. Cl.
| | | |
|---|---|---|
| *F01D 15/10* | (2006.01) | |
| *F24F 7/00* | (2021.01) | |
| *F24F 11/63* | (2018.01) | |
| *C07D 407/04* | (2006.01) | |
| *A61P 31/00* | (2006.01) | |
| *C07D 239/47* | (2006.01) | |
| *C07H 19/06* | (2006.01) | |
| *C07H 19/067* | (2006.01) | |
| *C07H 19/073* | (2006.01) | |
| *F24F 11/64* | (2018.01) | |
| *F24F 11/30* | (2018.01) | |
| *F24F 11/00* | (2018.01) | |
| *G01D 21/00* | (2006.01) | |
| *H02K 7/18* | (2006.01) | |
| *F24F 110/20* | (2018.01) | |
| *F24F 110/50* | (2018.01) | |
| *F24F 110/70* | (2018.01) | |
| *F24F 110/72* | (2018.01) | |
| *F24F 110/66* | (2018.01) | |
| *F24F 110/10* | (2018.01) | |
| *F24F 110/12* | (2018.01) | |
| *F24F 110/65* | (2018.01) | |

(52) U.S. Cl.
CPC ......... *C07H 19/067* (2013.01); *C07H 19/073* (2013.01); *F24F 11/0001* (2013.01); *F24F 11/30* (2018.01); *F24F 11/63* (2018.01); *F24F 11/64* (2018.01); *G01D 21/00* (2013.01); *G05D 7/0635* (2013.01); *H02K 7/1823* (2013.01); *F24F 2011/0002* (2013.01); *F24F 2110/10* (2018.01); *F24F 2110/12* (2018.01); *F24F 2110/20* (2018.01); *F24F 2110/50* (2018.01); *F24F 2110/65* (2018.01); *F24F 2110/66* (2018.01); *F24F 2110/70* (2018.01); *F24F 2110/72* (2018.01)

(58) Field of Classification Search
CPC ...... G01M 15/14; G01F 1/74; G01F 25/0007; G01F 1/8436; G01F 1/125
USPC .......... 701/100; 702/24, 34–35, 45, 50, 127, 702/182–183, 185, 188
See application file for complete search history.

(56) References Cited

U.S. PATENT DOCUMENTS

| | | | | |
|---|---|---|---|---|
| 5,251,815 A * | 10/1993 | Foye | ............... | G05D 7/0635 236/49.3 |
| 5,902,108 A * | 5/1999 | Nakayama | ............... | A61C 1/05 433/132 |
| 6,174,151 B1 * | 1/2001 | Yarr | ............... | F01C 1/103 137/469 |
| 6,257,073 B1 * | 7/2001 | Lee | ............... | G01F 1/10 73/861.91 |
| 7,642,692 B1 * | 1/2010 | Pulskamp | ............... | H01L 41/1132 310/309 |
| 9,157,645 B1 * | 10/2015 | Goss | ............... | F24F 3/0442 |
| 2003/0167919 A1 * | 9/2003 | Schempf | ............... | F17D 3/01 95/15 |
| 2004/0069069 A1 * | 4/2004 | Gysling | ............... | G01N 25/60 73/736 |
| 2004/0226386 A1 * | 11/2004 | Gysling | ............... | G01F 1/7082 73/861.42 |
| 2006/0105697 A1 * | 5/2006 | Aronstam | ............... | F24F 11/62 454/256 |
| 2007/0027638 A1 * | 2/2007 | Fernald | ............... | G01F 1/712 702/25 |
| 2007/0178823 A1 * | 8/2007 | Aronstam | ............... | F24F 11/0001 454/256 |
| 2008/0069699 A1 * | 3/2008 | Bech | ............... | B29C 66/721 416/229 R |
| 2009/0074578 A1 * | 3/2009 | Dewar | ............... | F03B 3/12 416/147 |
| 2009/0134631 A1 * | 5/2009 | Guerrero | ............... | E21B 41/0085 290/1 R |
| 2012/0006924 A1 * | 1/2012 | Ruola | ............... | D21D 1/306 241/277 |
| 2012/0087783 A1 * | 4/2012 | Zhang | ............... | F24T 10/10 415/180 |
| 2013/0341930 A1 * | 12/2013 | Campagna | ............... | F01D 15/10 415/17 |
| 2016/0197262 A1 * | 7/2016 | Zawada | ............... | H01L 41/1136 310/300 |
| 2016/0276573 A1 * | 9/2016 | Delamare | ............... | H02N 2/18 |
| 2017/0284219 A1 * | 10/2017 | Hunter | ............... | H02K 7/1823 |
| 2019/0121344 A1 * | 4/2019 | Cella | ............... | G05B 19/41865 |

FOREIGN PATENT DOCUMENTS

| | | |
|---|---|---|
| CN | 205489970 U | 8/2016 |
| DE | 102007012946 A1 | 9/2008 |
| DE | 102010028793 | * 10/2010 |
| DE | 102010028793 A1 | 11/2011 |
| FR | 2824907 A1 | 11/2002 |
| FR | 2930017 A1 | 10/2009 |
| FR | 2932552 A1 | 12/2009 |
| NL | 2013598 A | 8/2016 |
| WO | 2007/063194 A1 | 6/2007 |
| WO | 2009/153331 A1 | 12/2009 |
| WO | 2014/063951 A1 | 5/2014 |
| WO | 2014/063952 A1 | 5/2014 |
| WO | 2014/063958 A3 | 6/2014 |
| WO | 2016/146929 A1 | 9/2016 |

OTHER PUBLICATIONS

International Written Opinion for International Application No. PCT/FR2017/052814, dated Feb. 2, 2018, 06 pages.
International Search Report for International Application No. PCT/FR2017/052814, dated Feb. 2, 2018, 03 pages.
Flammini et al., "An autonomous sensor with energy harvesting capability for airflow speed measurements", Instrumentation and Measurement Technology Conference, May 3, 2010, pp. 892-897.
Dai et al., "Energy harvesting from mechanical vibrations using multiple magnetostrictive/piezoelectric composite transducers", Sensors and Actuators A: Physical, vol. 166, Dec. 31, 2010, pp. 94-101.
Chinese Office Action and Search Report from Chinese Application No. 201780062465, dated Dec. 30, 2020, 14 pages.
European Communication pursuant to Article 94(3) EPC for European Application No. 17794007, dated Mar. 11, 2021, 3 pages.

* cited by examiner

AUTONOMOUS DEVICE FOR MEASURING THE CHARACTERISTICS OF A FLUID CIRCULATING IN A CONDUIT AND SYSTEM FOR CONTROLLING VENTILATION, AIR CONDITIONING AND/OR HEATING USING SUCH A DEVICE

CROSS-REFERENCE TO RELATED APPLICATIONS

This application is a national phase entry under 35 U.S.C. § 371 of International Patent Application PCT/FR2017/052814, filed Oct. 12, 2017, designating the United States of America and published as International Patent Publication WO 2018/069656 A1 on Apr. 19, 2018, which claims the benefit under Article 8 of the Patent Cooperation Treaty to French Patent Application Serial No. 1659863, filed Oct. 12, 2016.

TECHNICAL FIELD

This disclosure relates to an autonomous device for measuring the characteristics of a fluid circulating in a conduit and, in particular, the characteristics of the flow of air circulating in a ventilation, air conditioning or heating conduit of a building. The disclosure also relates to a system for controlling the ventilation, air conditioning and/or heating of a building that uses such a device.

BACKGROUND

Modern buildings are all equipped with a ventilation, air conditioning and/or heating system that allows for the renewal of indoor air and the evacuation of stale air. This prevents the accumulation of excessive amounts of harmful compounds or particles: $CO_2$, volatile organic compounds, etc. Excessive humidity that can lead to building deterioration is also avoided, and a satisfactory level of comfort is provided for the residents.

As far as ventilation is concerned, and in general, the known solutions consist in drawing indoor air through conduits or pipes from the rooms likely to be the most humid (a shower room, a kitchen). Fresh air from the outside environment is introduced into the building, either naturally through openings (usually in the driest rooms) or by suction through ducts that allow a quantity of fresh air to be drawn from the outside.

Whatever the solution chosen, the renewal of the indoor air in a building is a source of energy loss. The outside air that renews the inside air generally has characteristics, especially in terms of temperature, very different from the inside air. This leads, as the case may be, to cooling or heating of the building, which must be compensated for by using additional heating or air conditioning to maintain air quality and indoor comfort.

In this context, integrated solutions are considered and aim to address all the issues related to heating, ventilation and air conditioning in a building in order to provide indoor air quality and expected comfort while keeping energy consumption as low as possible.

These integrated solutions require the installation of measuring devices (temperature, humidity, air quality sensors, etc.) to collect data characterizing the internal status of the building. The measuring devices are connected to a control device, such as a computer, so that the heating, ventilation and air conditioning equipment can be controlled. The control system also has the function of drawing up the control laws for these different means of achieving, with the lowest energy expenditure, the comfort instructions provided by a resident or a building manager and making it possible to comply with air quality constraints.

The collection of accurate and representative data on the condition of the building requires the installation of a sufficient number of measuring devices, and a homogeneous distribution of these devices throughout the building. This installation, the power supply of the devices, the necessary connections with the control device to be able to communicate the measured data require costly building layout work, especially when it comes to equipping an existing building. This presents a significant barrier to the deployment of such integrated solutions.

To solve this problem, it would be beneficial to have autonomous energy and communication measuring devices. Thus, the document "An autonomous sensor with energy harvesting capability for airflow speed measurements," Instrumentation and Measurement Technology Conference (I2MTC), 2010 IEEE proposes a measurement device seeking such autonomy. More specifically, this document discloses a device for measuring the speed of air circulating through a ventilation conduit. This device includes a fan set in motion by the air flow of the conduit, and connected to a dynamo that transforms the rotational movement of the fan into an electric charge. This charge is used to provide a measure of the flow of air circulating through the conduit. This document also specifies that the efficiency of a wind turbine increases with its speed parameter (also referred to as a feed parameter or specific speed, "Tip Speed Ratio") up to a theoretical limit value of 59%, and, therefore, encourages a rapid rotation of the turbine.

However, the laboratory solution described in this document is not suitable for a conventional building. It requires a high air flow speed, greater than 3 m/s, to provide sufficient energy for its operation. However, conventionally, the ventilation air flow can have a speed as low as 0.1 m/s. The system presented in the above-mentioned document cannot work under these conditions.

It should also be noted that for comfort reasons, the installation of ventilation, heating or air conditioning conduits with a large cross-section is encouraged in order to have, for a given flow rate, a lower speed of the air flow circulation. This flow can reach a fraction of 1 m/s. This limits the noise emissions associated with the high speed flow of the fluid through the conduit. Also, devices for circulating the fluid in the conduits (a pump or an extraction or a propulsion motor) that are less powerful and, therefore, more energy efficient can be employed in such a case. The system presented in the preceding document is, therefore, not suitable for the heating, ventilation and air conditioning systems of a modern building.

In addition, the measurement device proposed in this document provides for the transmission of the collected speed measurements to a receiver. To compensate for the small amount of energy collected, it is the receiver itself that provides the energy necessary for this transmission, by electromagnetic radiation. The receiver must, therefore, be positioned close enough to the measuring device to allow the efficient supply of energy, which is a major constraint.

German Patent Publication No. DE102010028793 also describes an energy autonomous device for measuring the characteristics of a fluid circulating in a conduit. This document recognizes the difficulty of setting a turbine of an energy recovery device in motion when the speed of the fluid in the conduit is low. It recommends increasing the speed of the fluid, for example, by locally restricting the diameter of the conduit, and thus allowing the energy recovery device to operate. However, in such a "fast" turbine operating mode, wear and tear and noise emission of the device are exacerbated.

A technology for energy recovery coupling magnetostrictive and piezoelectric materials is finally known from the document "Magnetostrictive piezoelectric composite structures for energy harvesting" by T. Lafont et al., published in the *Journal of Micromechanics & Microengineering*, Institute of Physics publishing, Vol 22, no. 9, 24-08-2012.

BRIEF SUMMARY

This present disclosure is intended to at least partially alleviate the problems described above. It aims, in particular, to provide a device for measuring a characteristic of a fluid circulating in a conduit that is autonomous in terms of energy. It also aims to provide a system for controlling the ventilation, air conditioning and/or heating of a building that is very simple and inexpensive to install. More specifically, the present disclosure relates to a device for measuring a characteristic of a fluid circulating in a conduit that has an extended operating time and low noise emission during operation.

In an effort to achieve one or more of these purposes, the subject matter of the disclosure proposes an autonomous device for measuring at least one characteristic of a fluid circulating in a conduit in a flow direction, the autonomous device comprising:
- a rotor comprising a turbine capable of being driven in rotation by the fluid, the rotor being assembled to a stator;
- attachment means for attaching the stator in the conduit or at one end of the conduit, in a configuration wherein the axis of rotation of the turbine is parallel to the flow direction;
- a permanent magnetic field source defining a magnetic plane perpendicular to the axis of rotation of the turbine;
- a magneto-electric converter having a reference plane and capable of transforming a variation in the reference plane of a magnetic field into a mechanical deformation capable of generating electric charges; and
- a processing circuit, electrically connected to the converter, and capable of exploiting electric charges to provide a measurement of a characteristic of its environment.

According to the disclosure, one of the converter and the source are included in the stator, and the other one is included in the rotor. The stator is connected to the rotor so that the reference plane of the converter resides in the magnetic plane generated by the source.

According to other advantageous and unrestrictive characteristics of the disclosure, taken alone or in any technically feasible combination:
- the source may be included in the rotor, integral with the turbine; and the converter may be included in the stator;
- the converter and the processing circuit may be included in the rotor, integral with the turbine; and the source may be included in the stator;
- the converter and the processing circuit may be arranged in a sealed housing;
- the turbine may be formed by a hub and a plurality of blades may be attached to the hub;
- the orientation of the blades may be adjustable or may be made of a flexible material;
- the stator may be at least partially housed in the turbine hub;
- the hub may have a hollow dome shape and an aerodynamic profile to accelerate the flow of the fluid to the blades;
- the hub may include a curtain that can clear a circulation passage for the fluid;
- the turbine may be designed to have a speed parameter of less than three;
- the turbine may have a strength between 0.7 and 1, and preferably close to 1.
- the blade setting angle may be between 15° and 45°;
- the blade setting angle may be variable;
- the converter may comprise, in its reference plane, a layer of magnetizable materials, and may be magnetically retained in the magnetic plane generated by the source so as to form a removable assembly between the rotor and the stator;
- a rotation shaft aligned with the axis of rotation of the turbine may be arranged between a centering unit placed on the rotor and a centering unit placed on the stator to guide the rotation of the rotor;
- the source may be formed by a plurality of magnets configured as Halbach cylinders; the axis of the cylinder being aligned with the axis of rotation of the turbine;
- the attachment means may include a conduit outlet, the rotor and the stator being placed inside the conduit outlet;
- the turbine may be equipped with a turbine identifier;
- the measurement of an environmental characteristic provided by the processing circuit may include at least one of the fluid speed, fluid flow rate, fluid temperature, $CO_2$ concentration, CO concentration, volatile organic compound concentration, and/or fluid moisture content;
- the device may include at least one sensor chosen from a temperature sensor, a $CO_2$ concentration sensor, a CO or volatile organic particle concentration sensor, a humidity sensor, and/or a turbine ID sensor;
- the processing circuit may include a charge pick-up circuit;
- the processing circuit may include a measurement transmission circuit;
- the processing circuit may include a device for storing the electric charges;
- the device may include means for modifying the flow of fluid circulating through the conduit;
- the means for modifying the flow of fluid circulating may be flaps or a curtain, the closing of which can be controlled to limit the passage section of the conduit; and
- the means for modifying the flow of fluid circulating may be flaps or a curtain, the opening of which clears a fluid circulation passage bypassing the turbine blades.

In another aspect, the disclosure relates to a system for controlling the ventilation, air conditioning and/or heating of a building, the building having a network of conduits, the system having:
- at least one autonomous measuring device; and
- a control device configured to process the measurement provided by the autonomous device and adjust the ventilation, air conditioning and/or heating status of the building.

According to other advantageous and unrestrictive characteristics of the disclosure, taken alone or in any technically feasible combination:

the control device also may be configured to provide maintenance or diagnostic information for the conduit network;

the control device also may be configured to configure the operating parameters of the autonomous device;

the control system also may include additional building sensors, such as room temperature or occupancy sensors;

the autonomous device may include means for modifying the flow rate of the fluid circulating in the conduit wherein it resides;

the control device may be at least partially integrated in the autonomous device to form a self-regulating device;

the control system may include a plurality of self-contained, self-regulating devices configured to communicate with each other;

the control device may be a computer, such as a smartphone, a tablet or a computer;

the control device may be located remote from the autonomous device, and the measurement provided by the autonomous device may be communicated to the control device via a long range network, such as the SIGFOX® network or the Internet.

BRIEF DESCRIPTION OF THE DRAWINGS

Other characteristics and advantages of the disclosure will emerge from the detailed description of the disclosure that follows with reference to the appended figures in which.

DETAILED DESCRIPTION

In order to simplify the description, the same references are used for identical elements or elements performing the same function in the various modes of implementation of the embodiments of the disclosure.

This present disclosure relates to an autonomous device for measuring at least one characteristic of a fluid circulating in a conduit and possibly modifying one or more of its characteristics. The device is autonomous in energy, and as such, it includes a generator that transforms the kinetic energy of the fluid into electric charges. The operating principles of the generator are described below.

Generator

Figure 1A:
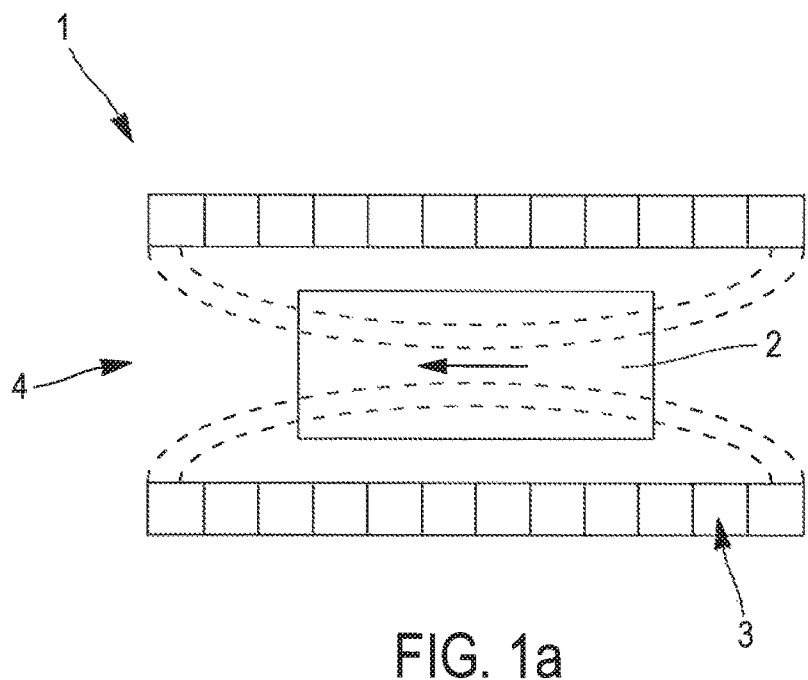
FIGS. 1a to 1c illustrate a generator according to different modes of implementation of the disclosure.
Figure 1B:
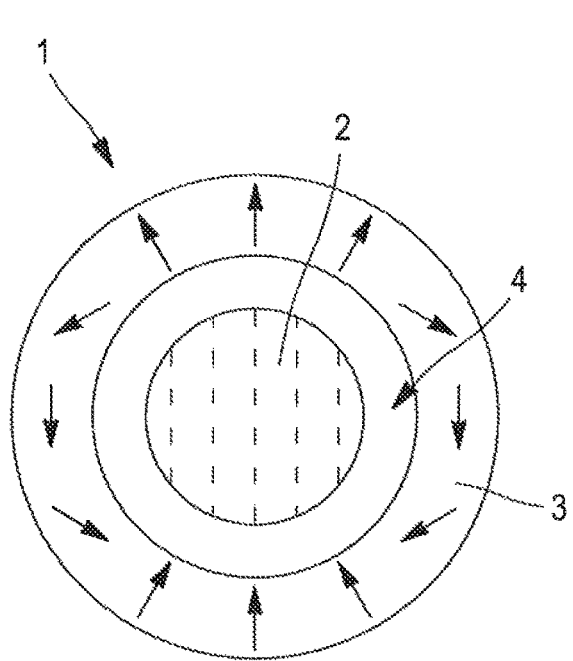
Figure 1C:
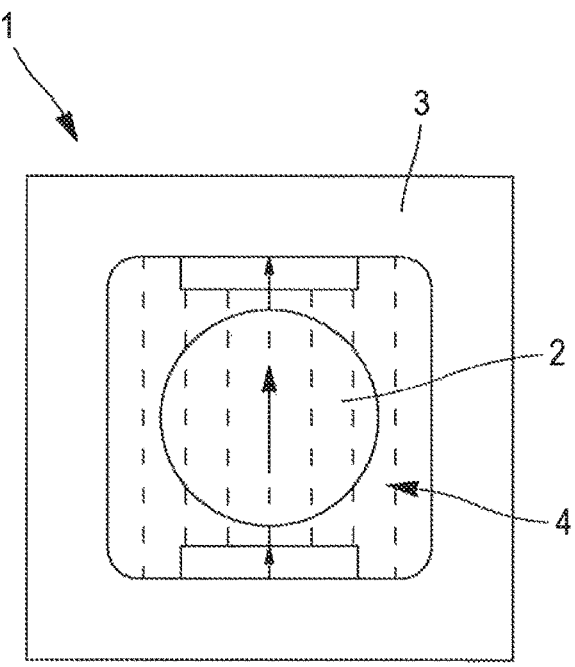

As shown as an example in FIG. 1c, a generator 1 operated by a non-limiting embodiment of the present disclosure includes a magneto-electric converter 2 and a magnetic field source 3, such as a permanent magnet. The converter 2 and the source 3 can move relative to each other. As will be explained in further detail below, the converter 2 can be kept stationary, and the source 3 can be rotated by a turbine driven by the fluid flow. Advantageously, the source 3 defines a housing 4 wherein the converter 2 can be placed and form a particularly compact unit. The charges supplied by the generator 1 are collected, and possibly stored using a sampling circuit associated with the generator 1. Such a circuit is known, for example, from WO2014063958, WO2014063952, WO2014063951, WO2016146929 or WO2007063194 and will not be described herein in greater detail.

Figure 2A:
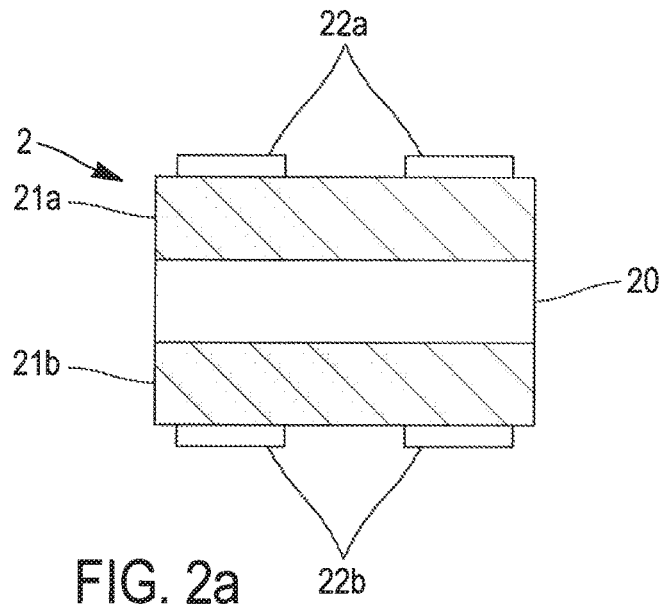
FIGS. 2a and 2b illustrate a schematic section and a top view of a converter.
Figure 2B:
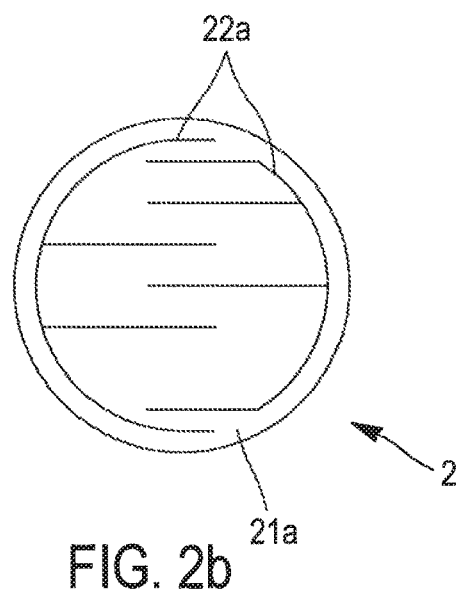

FIGS. 2a and 2b represent a particular example of a magneto-electric converter 2. The converter 2 is capable of transforming the variation of a magnetic field in a reference plane into a mechanical deformation capable of generating an accumulation of charges.

The converter 2 comprises a layer 20 of a magnetostrictive material preferably having a magnetostriction coefficient, in absolute value and at saturation, greater than 10 ppm, or greater than 30 ppm or even greater than 100 or 1,000 ppm. It should be remembered that this coefficient is defined by the quotient ΔL/L where ΔL is the elongation of the material in the presence of a magnetic field saturating the material, and L is the length of this material in the absence of a magnetic field.

Preferably, the material of the layer 20 is chosen to be inherently isotropic or to exhibit isotropic behavior in the generator 1. For example, it may comprise a crystalline or sintered Terfenol-D, Galfenol, Terbium Iron, Fer-Cobalt, Fer-Nickel or amorphous FeSiB block.

As shown in FIG. 2b, which is a top plan view of the converter 2, the layer 20 can have a disc shape. The layer 20 defines a reference plane for the converter 2 and the generator 1 wherein it is placed.

As is well known per se, the application of a magnetic field to the layer 20 in a given direction in the reference plane causes the layer to deform in that given direction (an elongation when the magnetostriction coefficient of the layer 20 is greater than 0).

The magneto-electric converter 2 also comprises, assembled integrally with the layer 20, at least one piezoelectric layer 21a, having electrodes 22a. In the example shown in FIG. 2a, two piezoelectric layers 21a, 21b are assembled on opposite sides of the layer 20. Each of these piezoelectric layers 21a, 21b has electrodes 22a, 22b at least on one side, for example, on the free (exposed) side thereof. As shown in FIG. 2b for the electrode 22a, the electrodes 22a, 22b can be interdigital electrodes configured to effectively collect the charges to be generated in each of the piezoelectric layers 21a, 21b.

The piezoelectric layer(s) 21a, 21b is/are preferably configured to operate in the $d_{33}$ mode, which is advantageously more sensitive than the $D_{31}$ mode. This helps to improve the performance of the converter. As the piezoelectric layers 21a, 21b are integrally joined to the magnetostrictive layer 20, the deformation of this layer 20 in the reference plane also causes the deformation of the piezoelectric layers 21a, 21b in a plane parallel to this reference plane.

The piezoelectric layers 21a, 21b are preferably polarized according to a polarization direction contained in the plane they define. When several piezoelectric layers 21a, 21b are present, they are advantageously arranged on the magnetostrictive layer 20 so that their polarization axes are arranged parallel to each other. It will be considered that this is the case in the coming description.

The deformation of the piezoelectric layers 21a, 21b according to their polarization directions leads to the creation of electric charges in these layers and their accumulation on the electrodes 22a, 22b. Such deformation is obtained when the magnetostrictive layer 20 is subject to a magnetic field, the orientation of which has a component parallel to the polarization direction of the piezoelectric layers 21a, 21b.

Figure 2C:
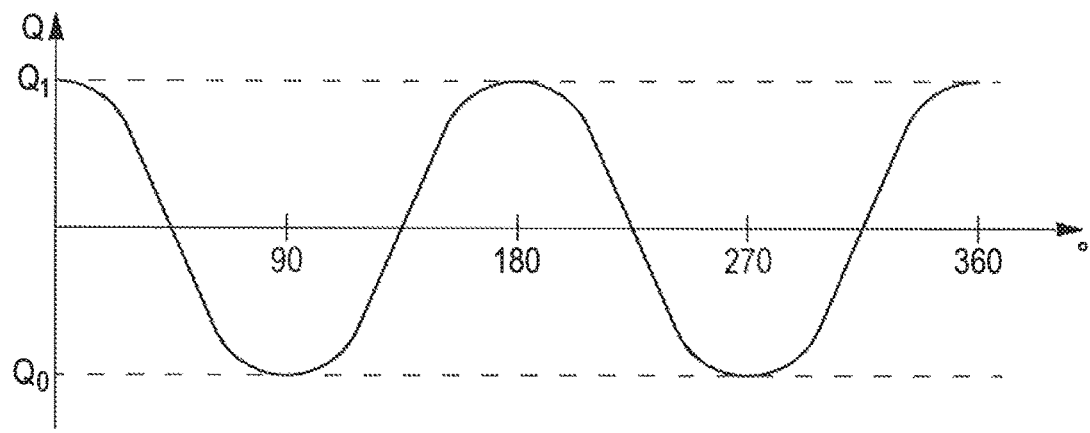
FIG. 2c is a graphical representation of the amount of charges generated by the converter as a function of the angle θ between the magnetic field direction and the polarization direction of the piezoelectric layers.

FIG. 2c is a graphical representation of the amount of charges generated on the electrodes 22a, 22b as a function of the angle θ between the direction of a uniform magnetic field developing in the magnetostrictive layer 20 and the polarization direction of the piezoelectric layers 21a, 21b. It can be seen that, in the absence of their collections, the accumulated charges oscillate between a maximum value $Q_1$ and a minimum value $Q_0$. The maximum value is reached when the angle θ is equal to 0° and 180°, i.e., when the directions of the magnetic field and the polarization axis are parallel. The minimum value $Q_0$ is reached when the angle θ is 90° and 270°, i.e., when the direction of the magnetic field and the polarization axis are perpendicular. Between two consecutive extremes, (positive or negative) charges are, therefore, created in the piezoelectric layers 21a, 21b.

Advantageously, when the converter 2 is subject to a rotating magnetic field, the sampling circuit is configured to collect the charges created at each quarter turn, for θ 0°, 90°, 180° and 270° angles.

As required, at least one of these quarter-turn collection steps may be omitted or these collection steps may be displaced angularly, for example, to reduce the induced braking torque, particularly when sufficient energy is available or when the drive torque is low, such as in low air flows as described in further detail below.

A magneto-electric converter 2 is thus formed and capable of transforming the variations, in the reference plane defined by the magnetostrictive layer 20, of a magnetic field into a mechanical deformation capable of generating an accumulation of charges on at least one electrode 22a, 22b of at least one piezoelectric layer 21a, 21b. The electrodes 22a, 22b can be connected to a terminal with which the sampling circuit can be connected.

It should be noted that the generator is by no means limited to a converter 2 of the precise form just described. Thus, a converter 2 comprising a single piezoelectric layer 21a or comprising a plurality of magnetostrictive layers may be employed in embodiments of the present disclosure. Similarly, the electrodes 22a, 22b may take other forms or be deployed differently from what has been described in the preceding paragraphs.

Returning to the description of FIGS. 1a to 1c, the generator 1 also includes a source of magnetic field 3. The magnetic field source 3 can define a housing 4 in which a magnetic field is present. In FIGS. 1a to 1c, this field is represented by the field lines in dotted lines. To limit the overall size of the generator 1 (e.g., of the order of one cubic centimeter, which is compatible with the aims of the present disclosure), the aim is to reduce the dimensions of the magnetic field source 3. The field strength can then be chosen in the range of 0.3 Tesla, or between 0.03 and 0.6 Tesla.

Preferably, the housing 4 and the source 3 are configured so that the converter 2 can be placed in the housing in such a way that at least a part of the field is placed in its reference plane. The source 3 and the converter 2 are free to move relative to each other, so that a rotating field can be created in the housing 4 opposite the converter.

Preferably, the field in the housing 4 is uniform, i.e., it has a relatively constant direction and/or intensity at least in a central part of the housing and preferably at any point of the housing. This makes it easy to place the converter 2 in the housing 4 without having to accurately position same in a particular location.

There are multiple ways to provide the magnetic field source 3.

According to a first approach, the source 3 consists of a flat assembly of permanent magnets oriented relative to each other so as to confine a magnetic field on one side of this plane. This assembly is well known as the "Halbach network."

By placing two of these assemblies opposite each other, with the fields facing each other, the housing 4 is defined as the space between these two planes. This configuration is shown in FIG. 1a. It should be noted, however, that it is not necessary to have two flat assemblies, and that a single assembly is sufficient to generate a useful magnetic field.

In a second approach, a plurality of permanent magnets are arranged relative to each other along a closed contour to define the housing 4 and create a field within it. For example, it may be a Halbach cylinder configuration, shown schematically in FIG. 1b.

As a complementary example, it can be a closed structure made of soft iron, defining the housing, two permanent magnets of identical magnetic moment are placed opposite each other in the housing as shown in FIG. 1c.

Regardless of the chosen configuration of the source 3, the converter 2 is placed opposite the source so that at least a part of the field is placed in the reference plane.

This disclosure takes advantage of the technological principles just presented to propose an autonomous device for measuring a characteristic of a fluid circulating in a conduit. Use of the generator for recovering energy from a fluid circulating in a ventilation conduit.

In some specific examples that will be described, the generator is used to recover energy from a fluid circulating through a ventilation conduit in a building. This fluid is, therefore, air. It should be noted, however, that the disclosure is certainly not limited to this type of conduit and fluid.

Air can be circulated in the conduit by suction or propulsion. The term "flow direction" will be used in the rest of the disclosure to generally refer to the direction of the fluid flow in the conduit section wherein the device is placed.

In the particular example of the ventilation conduits in a building, these can be a flexible conduit with a circular cross-section and a standard diameter of 50 mm, 90 mm, 125 mm or 300 mm. But a device in compliance with the disclosure is not limited to any particular size or shape of the conduit.

The usual ventilation rate of a building or residential apartment may be between 50 $m^3$ per hour and 200 $m^3$ per hour when it is not voluntarily controlled to a lower value. Standards may thus impose a particular flow rate according to the nature of the rooms, for example, a flow rate of 50 $m^3$ per hour for kitchen ventilation or 15 $m^3$ per hour for bathroom ventilation. The speed of air circulating through the conduits can be between a fraction of a meter per second, such as 0.05 m/s or 0.1 m/s or 0.5 m/s to several meters per second such as 4 m/s, 6 m/s or 10 m/s.

A device in compliance with the disclosure is operational in a wide range of air speeds, and ideally over the entire range from 0.05 m/s to 10 m/s, such as in the range from 0.1 m/s to 10 m/s, or from 1 m/s to 10 m/s or from 0.1 m/s to 4 m/s.

As will be discussed below, an autonomous device according to the disclosure extracts its operating energy from the flow energy of the fluid in the conduit, using a turbine. Per unit volume, this energy corresponds to the pressure difference $\Delta p$ generated on both sides of the turbine. In addition, the instantaneous power available on the fluid side takes the form $Q*\Delta p$, where Q is the volume flow rate of the fluid equal to the product $U*S$, where U is the average air flow speed in the section S conduit. It can be seen that for a given section, the instantaneous power available is highly dependent on the speed of the fluid. The ability to operate over a wide range of fluid speeds, especially at the lowest fluid speeds, is an advantageous characteristic of embodiments of the disclosure.

Autonomous Measuring Device

Generally speaking, an autonomous measuring device in accordance with the disclosure combines means for recovering the energy of the fluid circulating in the conduit and processing means for providing a measurement of at least one characteristic of this fluid. The energy recovered, using the generator, the operating principles of which have been previously discussed, is sufficient to supply energy to the entire processing system necessary to provide this measurement. The means are compact enough to be placed in the conduit or at one of the ends thereof.

Figure 3A:
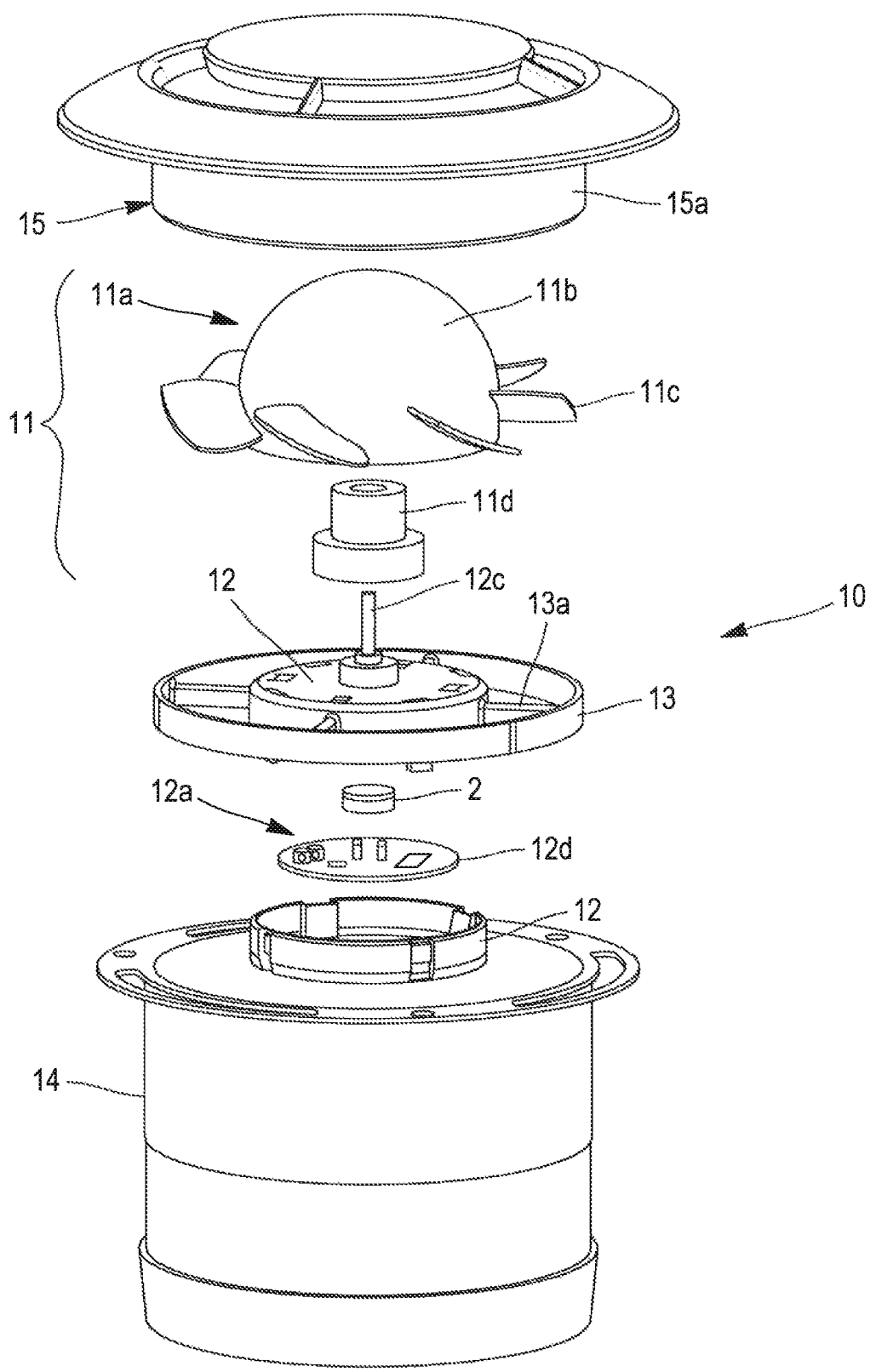
FIGS. 3a and 3b are respectively an exploded view and a sectional view of an autonomous device in accordance with the present disclosure.
Figure 3B:
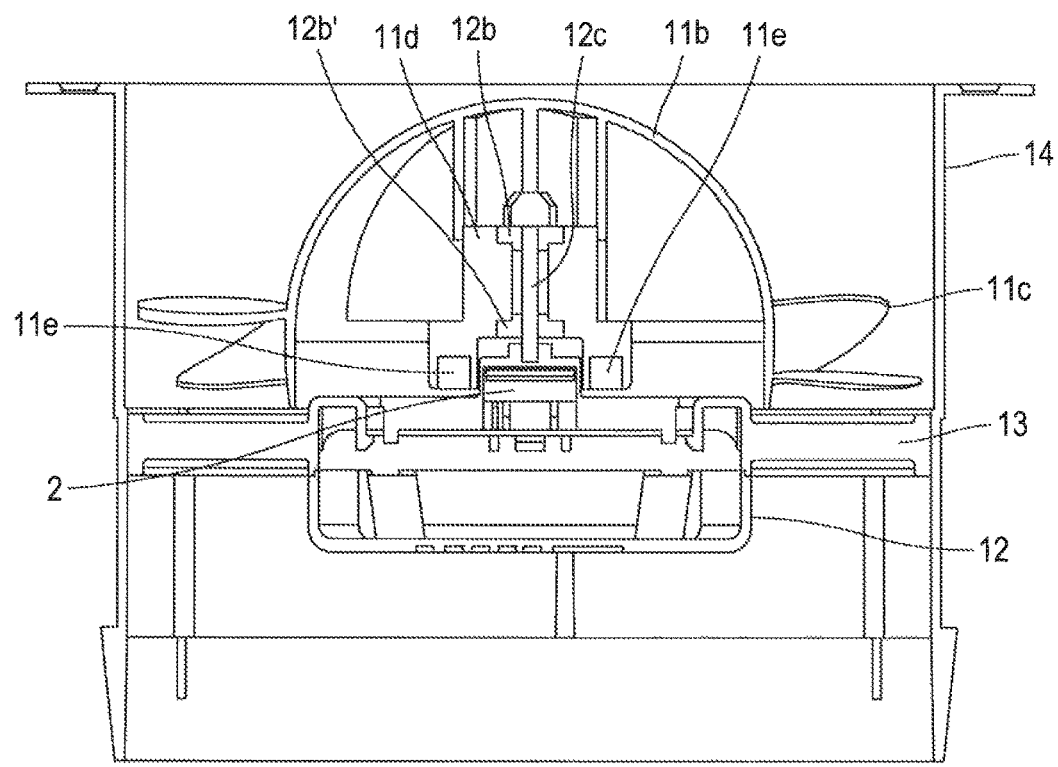

Thus, and as shown in the exploded view in FIG. 3a, and in cross-section in FIG. 3b, an autonomous device 10 in compliance with the disclosure is in the form of an assembly comprising a rotor 11, a stator 12, and attachment means 13 making it possible to position the stator fixedly in a conduit 14, or at one end of this conduit, and to orient the device in the flow direction.

The converter 2 may be placed in the stator 12, and the source 3 may be placed in the rotor. Alternatively, the converter 2 may be placed in the rotor and the source 3 may be placed in the stator. In other words, one of the converter 2 and the source 3 is included in the stator 12, and the other one is included in the rotor 11. For the sake of simplicity, only a detailed description of one of these embodiments will be provided.

The Rotor

The rotor 11 includes a turbine 11a that has an axis of rotation. The function of the turbine is to set the rotor 11 in rotational motion. When the autonomous device is properly assembled and held in the conduit 14 by the attachment means, the axis of rotation of the turbine is parallel to the flow direction. The turbine 11a is, therefore, capable of being driven in rotation by the fluid circulating in the conduit 14, and the circulating fluid is capable of setting the rotor 11 in motion.

The turbine 11a is designed to generate a torque higher than the resistive, static and dynamic torque, which opposes its movement, even at very low fluid speed, for example, less than 1 m/s. This resistive torque can include a friction torque originating from the possible friction of the rotor 11 with its environment when the rotor 11 is in motion. The resistive torque may also include a braking torque resulting from the energy conversion that occurs in the stator 12.

Advantageously, the turbine 11a is thus designed to form a slow turbine, i.e., its speed parameter w.r/v (where w is the angular rotation speed of the turbine, r its radius, and v the flow speed of the fluid) is less than three (3). A turbine 11a is thus available, which favors the development of a torque rather than obtaining a high rotational speed, and dedicated to the operation of very low flow rates.

More generally, the aerodynamic shapes of the turbine 11a are designed to promote low-flow aerodynamic torque while also limiting the rotational speed of the turbine in operation.

It is then possible to set the turbine 11a in motion for a reduced fluid speed, compared to the fluid speed required to drive a turbine with a speed parameter above three (3). In addition, a relatively low rotational speed of the turbine 11a (and, therefore, of the rotor 11) makes it possible to limit the noise emission of the autonomous device 10, which is an important parameter when it must be placed in a ventilation conduit opening into an office or bedroom. Finally, a low rotational speed also limits friction wear of the parts that make up the device. It should be noted that the choice of a turbine adapted to low air speeds and, in particular, with a speed parameter of less than three (3), is contrary to the teachings of the documents previously mentioned in the Background, which all seek, by different means, to place the generator in an operating mode corresponding to a fast rotor rotation speed, in order to make possible or efficient the energy conversion at the speed established using the conventional generators described.

The rotational speed of the turbine 11a and the rotor 11 are of course dependent on the fluid flow speed. For a relatively low speed, of the order of 1 m/s or less for air circulating in a ventilation conduit, it is possible to rotate the rotor at an angular speed of the order of 10 to 100 rpm, which is sufficient to provide the energy for operation of the device. In general, the turbine 11a of the rotor 11 is configured to achieve a rotational speed between 60 rpm and 1,000 rpm, preferably between 400 rpm and 800 rpm or 600 rpm, over a wide range of air speed in the conduit (e.g., between 0.1 m/s and 4 m/s). In these speed ranges, the energy recovered is sufficient to make the device autonomous, and low enough to limit wear and noise emission of the device. In addition to the adapted design of the turbine, and as will be explained in greater detail below, the search for such a relatively low rotational speed can lead to diverting part of the air flow from the conduit so that it does not contribute to the rotation of the turbine, in order to limit its speed at higher air speeds in particular. Finally, and as will also be described below, it should be noted that the mechanisms implemented in the generator of a device in accordance with the disclosure are particularly effective in recovering the energy supplied by slow and/or small amplitude movement.

As can be seen in FIG. 3a, the turbine 11a has a conventional architecture. It has a central hub 11b and a plurality of blades 11c attached to the hub 11b. This conventional architecture has very well established properties.

Advantageously, the hub 11b has a hollow dome shape with an aerodynamic profile. The dome has a vertex and a base that can be circular. The top of the dome is oriented in the conduit 14 upstream of the flow to take advantage of the aerodynamic profile. This is an attempt to preserve an essentially laminar flow of the fluid in the conduit 14, thus avoiding excessive pressure drops in this conduit. The aerodynamic profile of the free hub is also used to accelerate the flow of the fluid to the blades. The hub diameter can be chosen to be between 30% and 90% of the diameter of the turbine 11a (i.e., the distance between the ends of two diametrically opposed blades 11c).

Also advantageously, the turbine 11a has a strength between 0.7 and 1. It should be remembered that the strength of a turbine is the proportion of the surface of the disc swept by the turbine that is occupied by the surface of the blades and the hub. A high strength, close to 1, favors the development of a high torque, and is a preferred design choice.

However, a lower strength, for example, close to 0.7, can be chosen so that the presence of the autonomous device 10 in the conduit 14 does not excessively affect the flow of the fluid, and leads to excessive pressure drops in the conduit 14.

Preferably, the blades 11c are attached on the free hub to have a setting angle between 15° and 45°. This contributes to the formation of a slow wind turbine. In a very general way, the greater the angle of setting, the lower the rotation speed. For the sake of clarity, it should be remembered that the calibration angle is defined as the angle that a blade forms with the plane generated by the rotation of the blades. When the blade has a wing profile, this setting angle is the one formed by the string of this profile with the plane generated by the rotation of the blades.

According to an advantageous alternative solution, it is possible to make this angle of calibration variable and, possibly, controllable, for example, by means of the processing methods that are described further below.

Figure 5A:
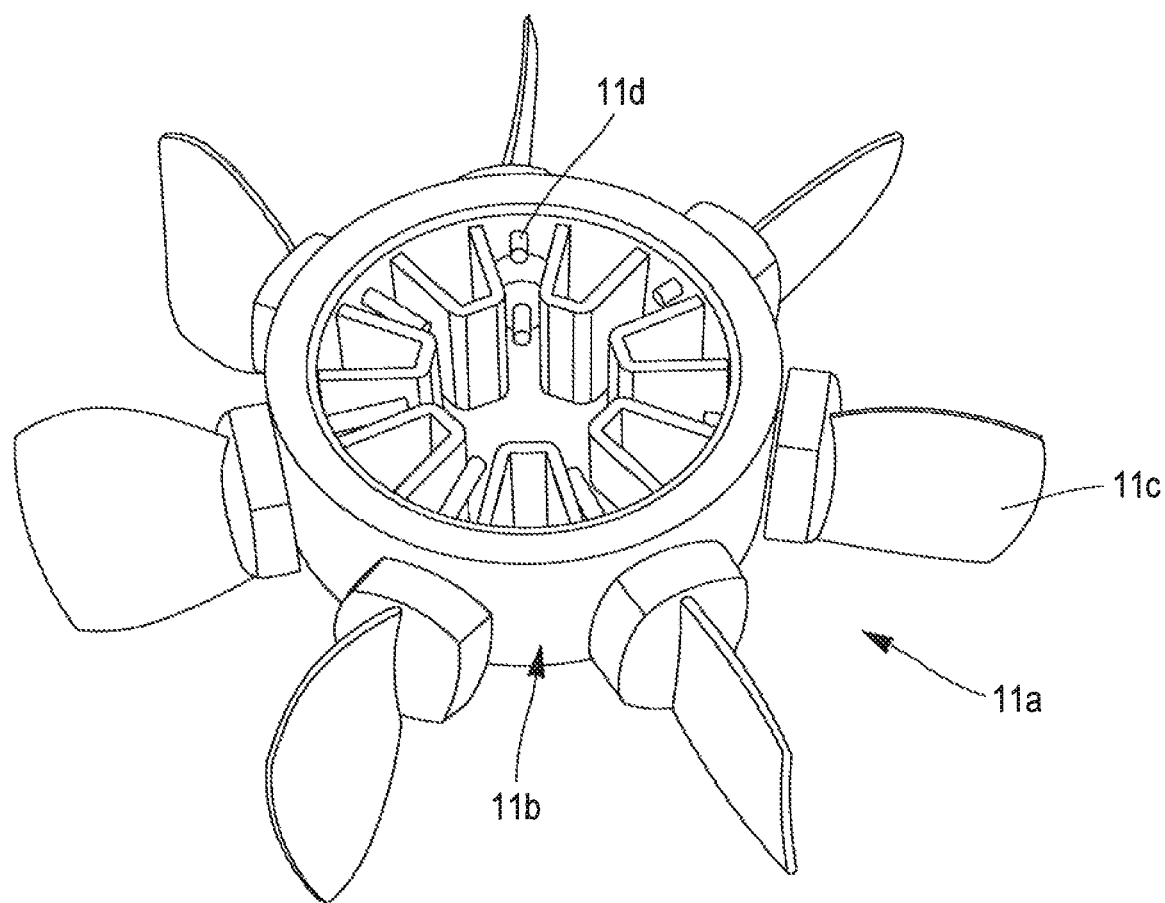
FIGS. 5a to 5e illustrate turbines that can be implemented in a device in accordance with the present disclosure.
Figure 5B:
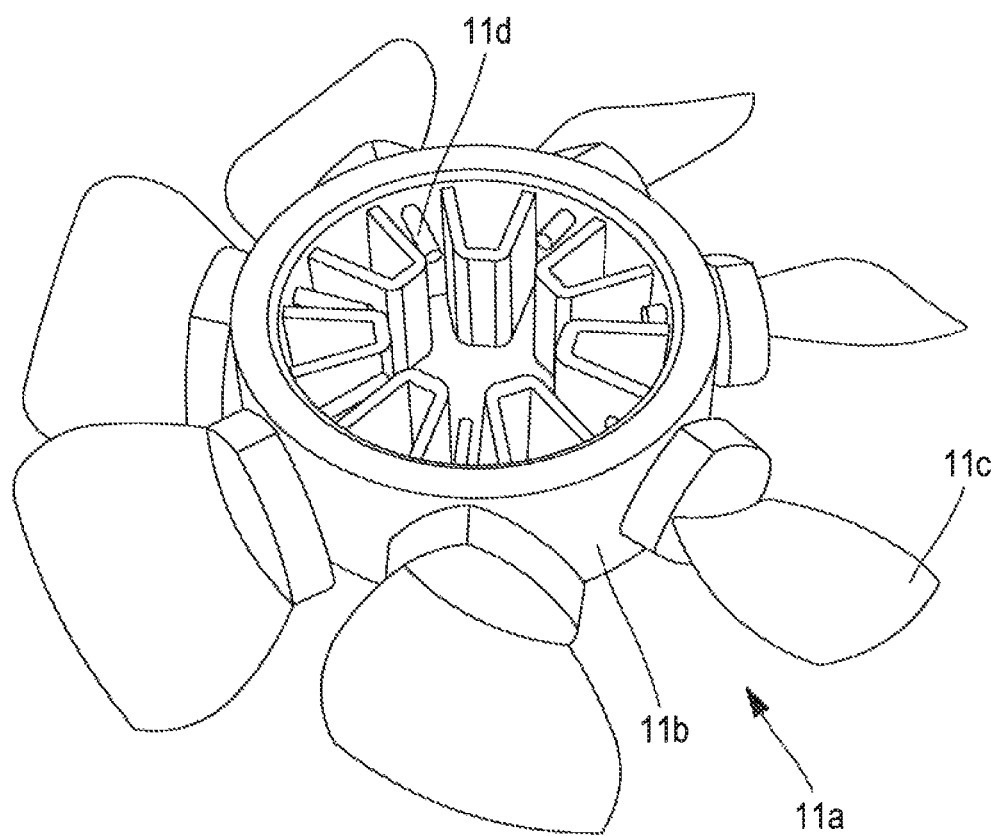

According to another alternative solution, it is possible to have a turbine 11a, the blades 11c of which can be selectively oriented according to a chosen calibration angle, in order to adapt, in anticipation, the device to its environment and the level of the fluid flow that is likely to pass through it. For example, FIGS. 5a and 5b show a turbine 11a on which the blades 11c are movably mounted to the hub 11b by means of a reversible attachment device 11d, and which enables the blades 11c to be axially oriented before the rotor is placed in a device according to the disclosure.

Figure 5C:
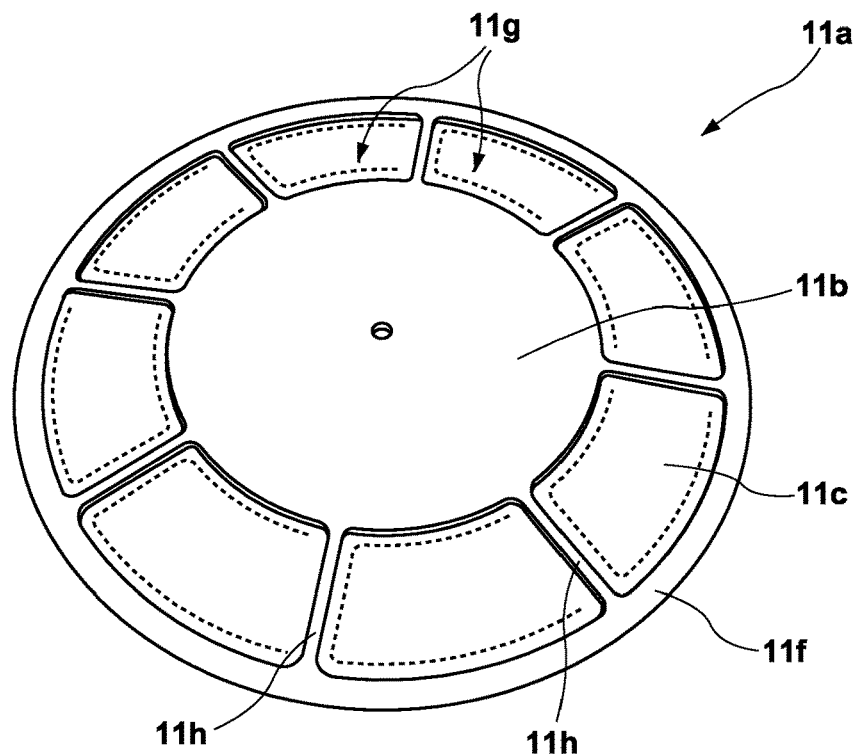

In yet another alternative solution, the blades 11c can comprise a soft or flexible material, the shape and angle of which is made variable according to the flow rate of the fluid circulating in the conduit. FIG. 5c shows such a turbine 11a, the free hub of which is connected via arms 11h to a retaining ring 11f, so as to form windows 11g. The blades 11c are made of a flexible plastic film held by the hub, the arms 11h and/or the crown or ring 11f. Cut-outs (in dotted lines in FIG. 5c) formed in the plastic film, at the windows 11g, along the arms 11h and/or the hub 1 1b and/or the ring 11f, define tabs that enable the film to deform under the pressure of the fluid flow in the conduit, so as to form blades 11c, the setting angle of which varies with the flow rate of this fluid.

By adopting one of the alternative solutions just described, it is possible to help control the turbine so that, in all fluid speed ranges, for example, between 0.1 m/s and 10 m/s, or 0.1 m/s to 4 m/s, the turbine does not exceed a rotational speed of 1,000 rpm, or 800 rpm or even 400 rpm.

More generally, it is possible to make the geometry of the blades variable, and to adjust this geometry to the fluid flow conditions, in order to favor the development of a high torque and a low rotation speed in any condition.

According to a first approach, the size of the turbine 11a is chosen to occupy the entire section of the conduit 14 when it is circular. In the case of a conduit of a different shape, the diameter of the turbine 11a can be chosen to correspond to the diameter of the circle inscribed in the section of the conduit 14. By thus occupying a maximum part of the passage section of the conduit 14, maximum use is made of the energy available and supplied by the fluid.

In an alternative solution, the size of turbine 11a is chosen to occupy only a portion of the conduit 14, the residual portion can be closed to constitute a restriction of the conduit section and force a higher air speed through the turbine 11a.

According to another alternative solution, an example of which will be given below, the residual portion is left free so as to allow a part of the fluid to circulate in the conduit without contributing to the rotation of the turbine 11a. This limits the rotational speed of the turbine, especially when the fluid speed is likely to be high.

In yet another alternative solution, the residual portion can be selectively opened or closed by a curtain or a flap.

Embodiments of the present disclosure are, of course, not limited to the turbine 11a just described, although it has shown satisfactory operation for a flow speed as low as 0.1 m/s, and has the advantage of a very low noise level, less than 35 dB(A) (for a fluid speed of 1 m/s).

A turbine 11a may be designed that will adopt an operating speed (i.e., a torque and a rotational speed according to the speed and nature of the fluid) best suited to the particular operating conditions of the autonomous device 10 (nature of the fluid, fluid speed range, size of the conduit passage section, impact of noise emissions). It is, therefore, possible to provide a device equipped with a first turbine particularly suitable to be positioned in a ventilation conduit (or at the end of this conduit) opening into a kitchen and, therefore, having a relatively high flow rate (and, therefore, an air speed), and to provide a second turbine, different from the first one, particularly suitable for placement in a ventilation conduit opening into a bathroom and, therefore, having a relatively low air flow and speed. Depending on the destination of the device, it may be chosen to equip same with the first or second turbine. In all cases, the turbine promotes a slow rotation of the rotor in order to limit noise pollution and device wear.

With reference to FIGS. 3a and 3b, the rotor 11 also includes a permanent magnetic field source 3 integral with the turbine 11a. In other words, the magnetic field source 3 is driven in rotation by the turbine 11a when it is in motion. The permanent magnetic field source 3 forms the field source of the generator 1, as previously described.

The permanent magnetic field source 3 defines a magnetic plane arranged perpendicularly to the axis of rotation of the turbine 11a. The magnetic field source 3 does not necessarily generate a field confined in a plane, and it is entirely consistent with the disclosure that the field generated by the source occupies a volume extending on either side of an average plane. In this case, the magnetic plane can be defined as this average plane.

For example, the source 3 can be made up of a plurality of magnets e. In a particularly advantageous configuration, the magnets 11e are assembled to form a Halbach cylinder, the axis of which is aligned with the axis of rotation of the turbine. As shown in the figures, the magnets 11e can be held together by a generally cylindrical body of the reversible attachment device 11d, which also enables the magnetic field source 3 to be fixedly connected to the turbine 11a.

The inside of the Halbach cylinder defines a housing wherein a uniform direction magnetic field is present, including the magnetic plane.

The sum of the magnetic moments of the magnets 11e forming the cylinder is zero, and the magnetic interaction of the cylinder with an external magnetic field is, therefore, zero or very low. Thus the earth's magnetic field or a magnetic source located near the device will create little or no torque on the device. This property ensures that the autonomous device 10 of the disclosure can be placed in conduits of any orientation (horizontal or vertical, for example) and placed near magnetic field sources without altering its operation or performance.

Whatever the shape of the permanent source of the magnetic field 3, the rotation of the rotor leads to the formation of a rotating magnetic field arranged at least in a plane perpendicular to the axis of rotation of the turbine 11a.

The Stator

The autonomous device 10 according to the disclosure also includes a stator 12. When the autonomous device 10 is in operation in a conduit 14, the stator 12 is fixedly held on the conduit 14 by means of the attachment means 13 so that it is not in motion.

One function of the stator 12 is to convert the energy of the rotational motion of the rotor 11 into sufficient electric charges to operate the autonomous device 10. For this purpose, the stator 12 includes a magneto-electric converter 2 as previously described herein. The converter 2, therefore, has a reference plane and a variation in the magnetic field in this reference plane leads to a mechanical deformation that can generate electric charges.

The stator 12 also includes a processing circuit 12a electrically connected to the converter 2. The processing circuit 12a is able to use the charges generated by the converter 2 to provide a measurement of a characteristic of its environment. This environment consists of air when the autonomous device is placed in a ventilation conduit.

The stator 12 is assembled to the rotor 11 so that the main plane of the converter 2 resides in the magnetic plane generated by the source 3. In this way, a generator 1 is formed that can transform the rotational movement of the rotor 11, due to the flow of the fluid in the conduit, into electric charges.

When the reference plane of the converter 2 includes a highly magnetizable layer, as is the case with the magnetostrictive materials presented in the introductory part of this description, the converter 2 is magnetically retained in the magnetic plane defined by the source 3. This forms a magnetic thrust bearing that supports the thrust transmitted by the turbine 11a.

This phenomenon, which leads to holding the rotor 11 and the stator 12 in parallel planes, can be exploited to allow an easily removable assembly of the rotor 11 and the stator 12. The rotor 11 can easily be separated from the rest of the autonomous device 10 by applying a force sufficient to extract the magnetic plane from its stable equilibrium position, aligned with the highly magnetizable layer.

This simple disassembly characteristic of the rotor 11 is particularly advantageous. For example, it is used to clean the grease and dust that could settle on the stator 12 and the rotor. It also makes it easy to reconfigure or maintain the device, for example, by replacing a defective or unsuitable first rotor with a second rotor that may have different characteristics relative to the first one. This maintenance can be performed without having to completely remove the autonomous device 10 from the conduit 14.

According to another advantageous characteristic of the disclosure, the rotor 11 can be equipped with a rotor identifier. This may be a magnetic or optical mark, an RFID circuit, or any other mark that identifies the rotor and its characteristics. The identifier can be identified by an optical sensor, or a magnetic sensor placed on or in the stator 12, enabling the presence of the rotor 11 and its characteristics to be identified. This information can be used by the autonomous device 10 to make the measurement.

An important characteristic of the autonomous device 10 according to the disclosure is that the braking torque resulting from the magnetic coupling that is formed between the stator 12 and the rotor 11 during the rotation of the rotor 11 is low in magnitude. In the case of an autonomous device 10 designed to measure at least one characteristic of the air circulating in a ventilation conduit (and, therefore, for a generator 1 that can occupy a volume of the order of 1 cm$^3$), this braking torque is less than 1 mN.m. In addition, this torque is essentially constant and independent of the rotational speed of the rotor 11. This very low braking torque helps to allow the turbine to rotate even at very low air speed, or more generally fluid speed.

The low speed rotation of the rotor 11 can also be promoted by placing a rotation shaft 12c between a first centering unit 12b arranged on the rotor 11 and a second centering unit 12b' arranged on the stator 12. The function of the shaft 12c is to guide the rotational movement and block the relative movement of the stator 12 and the rotor 11 in the plane perpendicular to the axis of rotation of the rotor. This limits the friction that can occur between these two elements. The shaft 12c and the centering units 12b, 12b' are aligned with the rotation axis of the turbine 11a. The nature of the materials forming the centering units 12b, 12b' and the rotation shaft 12c is chosen for its resistance to friction wear. For example, it can be a shaft made of steel (preferably stainless steel or non-magnetic) or plastic (POM, Teflon, etc.) combined with centering units made of plastic (POM, Teflon, etc.), metal (bronze, brass, etc.) or stone (ruby, etc.). A bearing system, such as a ball bearing system, can also be employed to facilitate the rotation of the rotor.

Alternatively to this configuration, a device can be provided for the purely magnetic centering of the stator 12 and the rotor 11, or a magnetic centering device can be combined with a mechanical stop bearing. In all these configurations, the easily removable nature of the stator 12 and rotor 11 assembly is preserved.

To make the autonomous device 10 very robust, the stator 12 can include or form a sealed housing wherein the converter 2 and the processing circuit 12a are placed. Very moist air can circulate in the conduit, especially when it is a ventilation conduit, and thus the most fragile parts of the autonomous device 10 may need to be protected. In the alternating mode of implementation wherein the converter 2 and the processing circuit 12a are placed in the rotor, it may be expected that this element will be made up or include a sealed housing. Advantageously, the assembly of the converter to the sealed housing and the processing circuit is carried out by means that at least partially absorb the vibrations or noise emissions that may be emitted by the converter, in particular, during the sudden deformation of the materials that occurs when the charges are picked up. This helps to limit the noise emissions of the device during operation.

To ensure that the stator 12 does not form an interfering element for the fluid flow, it can be given a shape compact enough to be housed in the hub 11b of the turbine 11a. This is particularly the case when the turbine 11a has a dome-shaped hub 11b with a wide base to accommodate the stator 12, as shown in the cross-sectional view in FIG. 3b. This helps to limit or avoid a pressure drop in the conduit.

For economic and compactness reasons, the converter 2 and the processing circuit 12a can be placed on a single substrate 12d, for example, of the PCB type. The substrate 12d can be equipped with conductive tracks to electrically connect the converter, for example, at its connection terminal(s), and the other elements of the processing circuit 12a.

The processing circuit 12a includes a circuit for taking the charges supplied by the converter. This circuit can be configured to, for example, take four energy pulses upon each rotation of the rotor 11. The sampling circuit may include a device for storing electric charges, such as a battery or capacitor, in order to provide a stable source of energy for a sufficient period of time to develop and provide the measurement.

Figure 4:
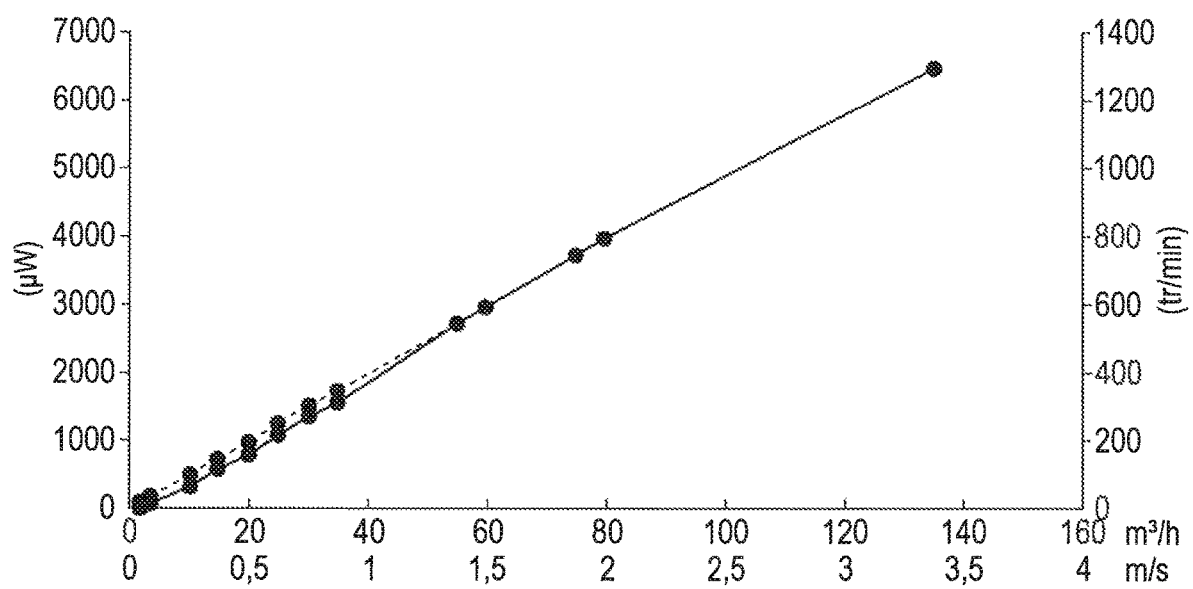
FIG. 4 is a graph correlating the air flow speed in a ventilation conduit to the rotor rotation speed and the power generated by the generator.

For example, FIG. 4 shows a graph of the power generated (left y-axis) by a generator consisting of a rotor and a stator as described above. This device has been designed to provide a measurement of the air flow in a 125 mm diameter conduit. It can be seen that for air speeds between 1 m/s and 3.5 m/s (abscissa axis), the stator is driven in rotation at a speed up to about 1,200 rpm. This speed can generate up to 6 milliwatts of power. This level of energy is sufficient to enable the operation of an autonomous device 10 in compliance with the disclosure and, in particular, to supply power to the processing circuit. This energy level may also be sufficient to supply a possible actuator, for example, a restrictor or flow enhancer in the conduit, as will be discussed in greater detail below.

Advantageously, the processing circuit 12a includes a transmission circuit for transmission of the acquired measurements. It can be a radio transceiver circuit, for example in BLUETOOTH®, ZIGBEE®, ZWAVE®, ENOCEAN® or SIGFOX® format. The nature of the format chosen is dictated by the required range of the transmission circuit, and the distance between the autonomous device and a receiver.

The general function of the processing circuit 12a is to provide at least one measurement of a characteristic of its environment. When it is placed in a conduit wherein a fluid flows, its environment includes the fluid circulating in the conduit.

Thus, according to a first aspect, the processing circuit 12a may be configured to take a measurement of the fluid speed. This measurement can be easily obtained from the measurement of the rotor 11 rotational speed or the power generated, using a table or a correlation relationship linking the turbine rotational speed or the power generated to the fluid speed. Such a relationship is shown as a dotted line on the graph shown in FIG. 4.

The processing circuit 12a is configured to determine the speed of rotation of the turbine/stator. The energy pulses generated by the converter 2 can be used to obtain this rotational speed for each determined fraction of a revolution of the rotor 11 rotation. Thus, the rotational speed of the rotor 11 can be determined by measuring the time between two successive pulses.

Advantageously the measurement of the fluid speed will be based on the rotation speed of the rotor 11. This determination method is more reliable than the one based on the power supplied by the generator 1. Indeed, the power delivered can vary according to the particular conditions of the environment (temperature, humidity, degree of wear, etc.), which affect the efficiency of the generator over time, i.e., the relationship between the power generated and the speed of the fluid. This is not the case with a method based on the time between two energy pulses.

It should also be noted that the fluid speed measurement can be provided, when the autonomous device 10 is placed in the conduit, without necessarily equipping this autonomous device 10 with a separate sensor specific to acquiring such a measurement. The properties of the energy generator 1 are used to acquire this measurement.

As the correlation relationship may be dependent on the characteristics of the turbine 11a or more generally of the rotor 11, the processing circuit 12a can be configured to select the correlation table or the relationship corresponding to the turbine 11a or the rotor 11 actually placed on the autonomous device 10. To this end, it will be possible to use the rotor identifier, if any, to make this selection automatically, as previously discussed.

To carry out the above-mentioned processing operations, the processing circuit 12a includes, on a substrate 12d, discrete or integrated electronic components enabling the described functions to be carried out. Advantageously, the processing circuit 12a can include one or more programmable computers such as a micro-controller or a microprocessor dedicated to signal processing.

In some cases, it may be advantageous to equip the autonomous device 10 with at least one additional sensor. This takes advantage of the available energy to provide a plurality of fluid characteristics, or other information not directly related to the fluid itself.

The autonomous device 10 can thus be equipped with a temperature, humidity, $CO_2$, CO, or volatile organic particles sensor to provide characteristic fluid measurements. When the conduit is an extraction ventilation conduit, these measurements can correspond to the atmosphere in the room from which the air was drawn. This makes it possible to deduce information that can be used for integrated control of ventilation, heating and/or air conditioning, or even room lighting, opening and closing flaps or any other home automation control.

The autonomous device 10 can also be equipped with sensors that do not directly try to measure a characteristic of the conduit flow. Thus, and insofar as the autonomous device 10 is placed near the end of the conduit, it may be necessary to provide this autonomous device 10 with an occupancy or temperature sensor for the room wherein the conduit opens. This is particularly possible when the autonomous device is integrated into a conduit outlet 15, attached to the end of a conduit and, therefore, having direct access to the room.

These sensors can be connected to the processing circuit 12a by wire connections. Alternatively or in addition, the autonomous measuring device 10 can also be connected to sensors via a wireless reception circuit of the processing circuit 12a. The autonomous device 10 can then be connected to sensors placed directly in the part, the characteristics of which are to be accurately measured.

The autonomous device 10 can also be connected to a control device, such as a mobile phone, a tablet or a computer or any other form of computer to be configured or diagnosed. This connection can be provided by the transmission circuit of the processing circuit 12a. This may include, for example, specifying the characteristics of the rotor 11, if the device does not have the automatic identification functionality described above.

To best manage the available energy, it is not necessary for all fluid characteristics to be established and provided at a fixed frequency. It is, therefore, possible to decide to establish a first characteristic (e.g., a fluid speed measurement) according to a first measurement frequency, and to establish a second characteristic (e.g., a $CO_2$ or CO concentration measurement) at a second frequency, lower than the first. In general, the frequency of the measurement of a characteristic is chosen to be adapted to the dynamics of the measured phenomenon.

Nor is it necessary to transmit a measurement directly after it is obtained. A measurement can be temporarily stored in a memory of the processing circuit 12a and transmitted at a frequency that may be different from the measurement frequency. The quantity, nature and frequency of readings and transmissions can also be determined automatically to make the most of the energy supplied by the generator.

Attachment Means

The attachment means 13 enable the autonomous device 10 to be retained in the conduit 14 in an operating position. In this position, the axis of the turbine 11a is parallel to the flow direction of the fluid. Preferably, the attachment means 13 must hold the autonomous device 10 sufficiently so that it can be positioned in the conduit regardless of the orientation of the conduit, for example, horizontal or vertical.

For example, the attachment means 13 may include a frame, connected to the stator by branches 13a, the frame having an outline, at least part of the outer surface of this outline being supported on the inner surface of the conduit 14. For example, the frame may have a circular contour, the diameter of which corresponds to the diameter of the conduit. This configuration is the one shown in FIGS. 3a and 3b.

In an alternative solution, the attachment device 13 includes a conduit outlet 15, and the rotor 11 and the stator 12 are at least partially arranged in the conduit outlet 15. The outlet can have a sleeve 15a, the shape and size of which are adjusted to the shape and size of the conduit 14. By inserting the end of the sleeve 15a into the conduit 14, the conduit outlet 15 is attached to the conduit 14. The rotor 11 and the stator 12 can be arranged, at least in part, in the sleeve 15a. This forms an autonomous device 10 that can be installed very simply by a user by replacing an existing conduit outlet with an outlet that includes an autonomous device 10 in accordance with the disclosure.

In addition to its function of providing at least one measurement, the autonomous device 10 according to the disclosure can also be configured to modify or control one of the characteristics of the fluid or its environment. For example, the processing circuit 12a can be configured, after analyzing the obtained measurements, to automatically control the heating, cooling or ventilation equipment. In the particular example where the autonomous device 10 is located in a ventilation conduit, it may be necessary to open a window if the measurement provided indicates poor air quality, such as excess humidity or $CO_2$. It could also include controlling a room heater if the ventilation air flow measurement shows a temperature below a comfortable temperature.

The processing circuit 12a can also be configured to control other types of devices. For example, this may be the control of a visual or audible alarm in the event of smoke detection.

Advantageously, the controlled device that makes it possible to modify or control one of the characteristics of the fluid or its environment can be part of the autonomous device 10 itself. For example, it may be a device implementing means to modify the flow of the fluid circulating through the conduit. For example, the autonomous device 10 may include a flap or a curtain, the controlled movement of which enables the passage cross-section of the conduit to be modified. The flap or curtain can be made of a piezoelectric material (PVDF), for example, the deformation or shape of which can be controlled by applying a voltage. The flap and/or curtain can be integrated into the attachment means 13, the opening or closing movement of the flap or curtain can be guided by the support frame.

According to a first approach, the flap or curtain can be arranged in series with the rotor, i.e., upstream or downstream thereof. In this case, the autonomous device 10 can then reduce or even completely interrupt the flow of fluid in the conduit and, for example, reduce or interrupt the ventilation of a room according to the circumstances established by the measurements provided.

To enable this embodiment, the device can include a control device integrated into the processing circuit 12a. Advantageously, the integrated control device (if not already provided for in the processing circuit) should include an element for storing electric charges, such as a battery or capacitor, to be able to store the energy required to operate the controlled device. The storage device is particularly useful for controlling the opening of the device and restoring the circulation of the fluid (because in the event that the circulation of the fluid is interrupted, generation of energy is no longer possible). Alternatively, the controlled devices can be designed so as to be "normally open," i.e., in the absence of energy supply, these devices are biased to a configuration in which the flow of fluid is not completely interrupted. Whatever the solution implemented, an autonomous and self-regulated device 10 is then available.

Another particularly advantageous approach is that the flap or curtain can be placed in parallel with the rotor, i.e., it can close or clear a fluid bypass passage, bypassing the turbine blades. A fluid flow path can thus be opened, without the fluid prompting the rotation of the rotor. This mechanism is particularly advantageous when it is desired to maintain a low rotor speed, for example, less than 1,000 rpm or 800 rpm despite a relatively high air flow rate. As already mentioned, a low rotational speed is favorable for reducing wear of the device and its noise emission.

Figure 5D:
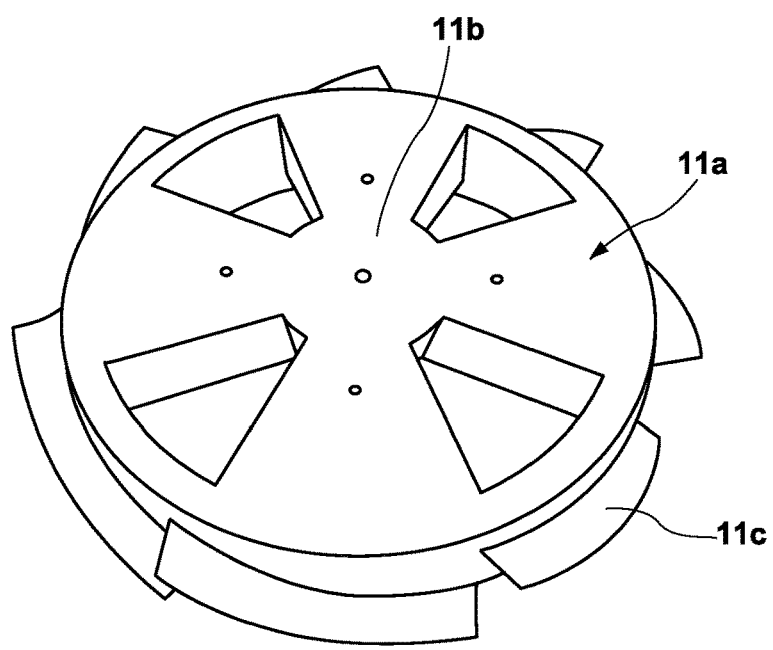
Figure 5E:
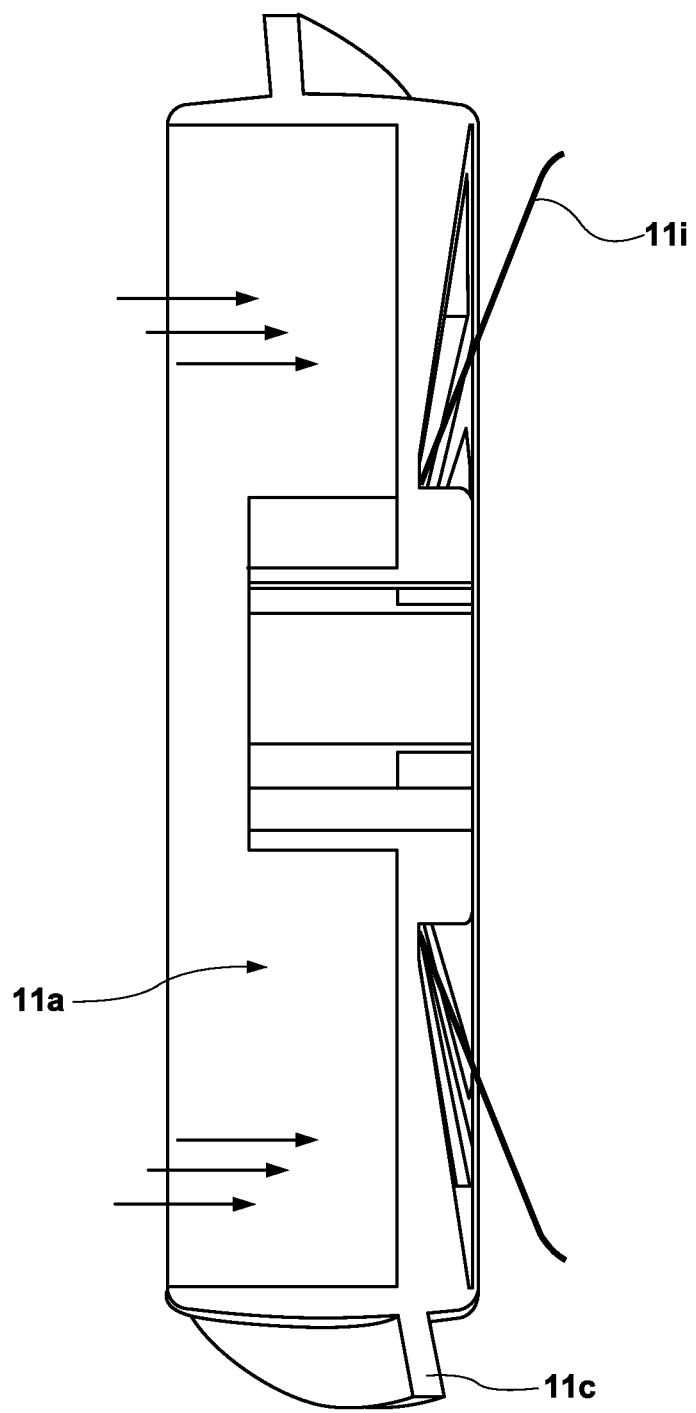

It is not necessary for the opening of the curtain or flap, in this other approach, to be controlled. As such, FIG. 5d (in perspective) and FIG. 5e (in cross-section), show a rotor 11, the hub of which is equipped with a flexible plastic curtain 11i. This curtain 11i (particularly visible in FIG. 5e) may deform under the effect of the flow of fluid circulating through the conduit so as to clear a passage enabling the fluid to flow without contributing to driving rotation of the rotor. The higher the fluid flow rate, the more the curtain tends to open to allow the fluid to flow through this bypass passage. It should be noted that this mode of implementation makes it possible to provide a bypass passage without affecting the flow rate of the fluid in the conduit. It can be expected that the curtain will be pre-stressed, and that it will only deform when the flow exceeds a given value.

Figure 6:
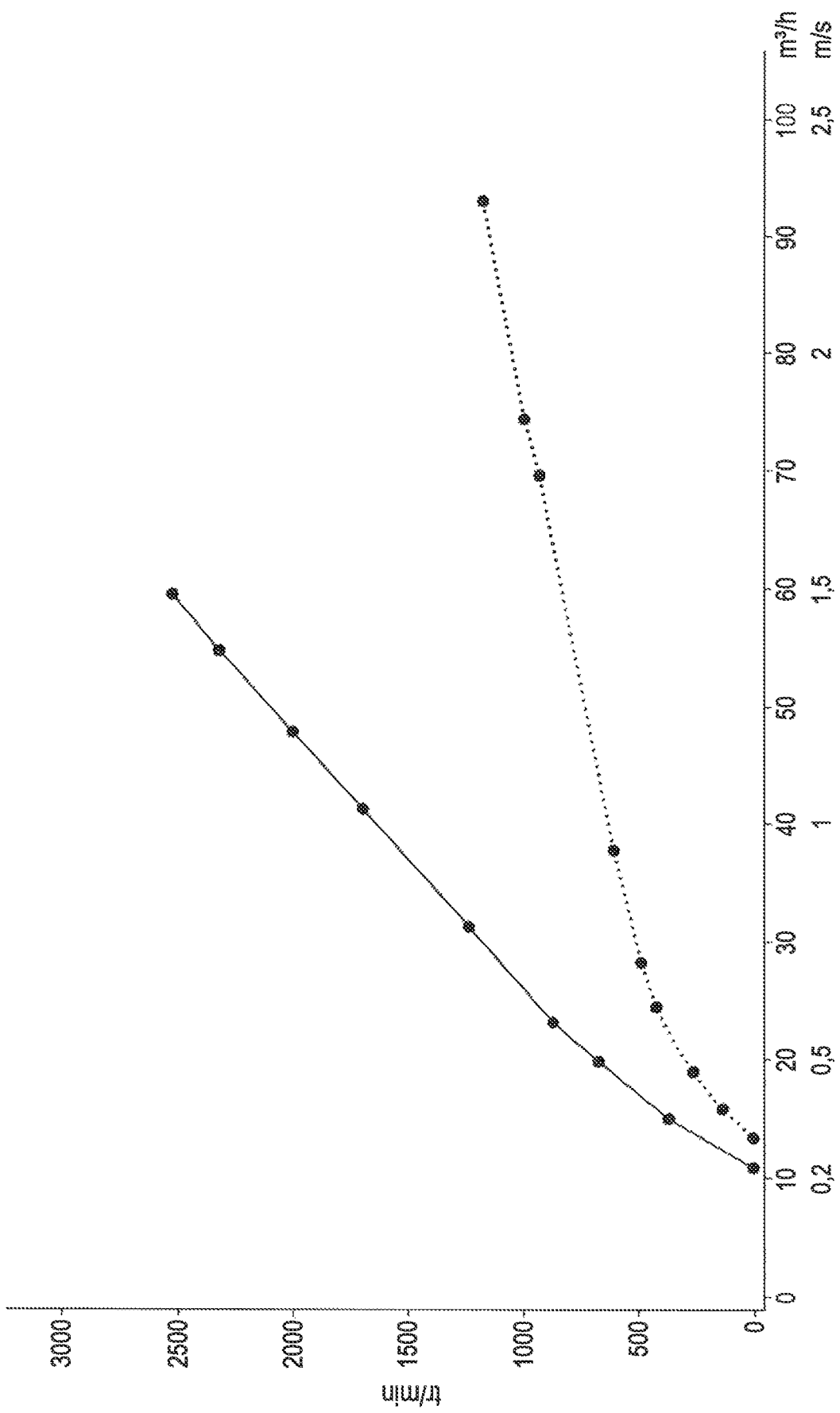
FIG. 6 is a graph correlating the rotational speed of a turbine of a device in accordance with the disclosure to the speed of the fluid circulating in a conduit.

FIG. 6 shows the rotational speed according to the air flow rate of a turbine placed in a 125 mm diameter conduit with a solid central hub (solid line) and a turbine with a central means with such a flexible curtain (dotted line). It can be seen that the rotational speed is significantly reduced in this second configuration, for all air flows. It should be noted that it is possible to maintain the rotation speed below 1,000 rpm for a wide range of air flow rates. More than 3 dB(A) of noise emission reduction was observed in the second configuration compared to the first at 50 $m^3$/hr.

Control System.

The autonomous device 10 for measuring a characteristic of a fluid circulating in a conduit can be used in a control system for ventilation, air conditioning and/or heating in a building. The building can be a residential building or an industrial or office building. As is customary, these buildings have a network of conduits, wherein fluids, usually air, circulate to perform the functions mentioned above.

For example, the network may consist of a first heating and air conditioning network making it possible to inject heated or cooled air into the rooms of the building, and a second ventilation network making it possible to extract air from these rooms to allow its renewal. According to an advantageous aspect, at least one autonomous device 10 may be placed in one and/or the other of these networks.

A control system in accordance with the disclosure, therefore, includes at least one autonomous measuring device 10 in accordance with one of the alternative embodiments previously described herein. The autonomous measuring device 10 is positioned in a network conduit in an operating configuration using the attachment means 13. In some embodiments, a plurality of these autonomous devices 10 will be placed in a plurality of conduits, so as to have sufficient information to finely control the level of comfort and air quality of the building. This may include, for example, placing an autonomous device 10 in each of the injection and extraction conduits in the network near the rooms serviced in the building.

The control system in accordance with the disclosure may also include at least one control device for adjusting the ventilation, air conditioning or heating status of the building. The control device receives and processes the measurements provided by the autonomous device(s) to control the heating, air conditioning or ventilation means of the building in order to achieve a specific level of comfort and air quality. This level can be chosen by a resident, an occupant and/or a building manager.

According to an alternative solution, the autonomous device 10 includes means to modify the flow of the fluid circulating in the conduit in which it is placed. The control device is capable of controlling these means, for example, to increase or reduce the air flow rate in a ventilation, heating and/or ventilation conduit. The control device can then, to a certain extent, control the status of the building without necessarily using or resorting to the available ventilation, heating or air conditioning resources. The control system may, in this alternative solution, be able to provide a "total rest" configuration or mode, by activating the means to modify the flow of the fluid to completely interrupt the flow, and switching off or putting into a standby mode the heating, air conditioning and/or ventilation system, such as pumps, heat exchangers, etc., in the building. This enables the building to be placed on standby for extended periods of time. Alternatively, it may be planned to, for safety reasons, shut off or reduce the operation of the heating, air conditioning and/or ventilation system, when a large number of autonomous devices have implemented the means to modify and, in particular, limit, the flow of the fluid in order to avoid excessive stress on these systems when the air flow to be circulated is limited.

The control system may also be coupled with other measurement sensors, such as room temperature sensors or room occupancy sensors, in order to develop a control system without relying only on the measurements provided by the autonomous device(s) 10.

The control system, and more particularly the control device, is advantageously configured to provide diagnostic or maintenance information for the conduit network. The information provided by the autonomous devices 10, such as flow information, can be used to identify leaks or pressure drops, such as excessive fouling or damage to a conduit.

As mentioned above, at least some of the functionalities of the control device can be integrated into the autonomous device. In this case, the processing circuit 12a of the autonomous device 10 includes a transmission circuit with transmission-reception capabilities, enabling it to exchange information. This information can, for example, be exchanged with other autonomous devices 10 in the system, in particular, those concerning the ventilation, air conditioning and/or heating status of the building. The processing circuit 12a of each of these autonomous devices can be configured to use the information received. This forms a distributed control system, which does not necessarily require a control device with a centralized part or a concentrator to be operative.

Generally speaking, the control device can be a computer. When at least partially integrated into an autonomous device, the ECU may be that of the processing circuit 12a.

When the control device includes a centralized part or a concentrator, the ECU may be a computer, a mobile phone or a tablet. The centralized control device or concentrator is not necessarily located in the building equipped with the autonomous device(s) 10. It can thus be expected that the measurements provided by the autonomous device 10 will be directly or indirectly addressed to the centralized control device or the concentrator via a long-distance network, such as the SIGFOX® network or the Internet network. It is then possible to control, from a centralized station, the ventilation, heating and/or air conditioning status of a park of buildings. A large-scale energy saving strategy can thus be set up, for example, by implementing a charge-shedding strategy making it possible to reduce the level of comfort during certain time slots (night, weekend, holidays) in order to better manage the energy consumption of the buildings.

Of course, the disclosure is not limited to the mode of implementation described and alternative embodiments can be provided without going beyond the scope of the invention as defined by the claims.

Although, in some examples, the measurement of a characteristic of the air circulating in a ventilation conduit has been taken, the disclosure is certainly not limited to this application. Thus, the device in accordance with the disclosure can be used to provide a measurement relating to a fluid circulating in any conduit of a network of conduits in a building. This can be, for example, an air conditioning or heating conduit, wherein cooled or heated air circulates.

Nor is the autonomous device 10 in compliance with the disclosure limited to a gaseous fluid. It can be a liquid fluid, such as water, circulating through a supply conduit.

And the disclosure is by no means limited to an application in the building industry. It can be used in a general way to make the measurement of a characteristic of any fluid circulating in any conduit.

The invention claimed is:

1. An autonomous device for measuring at least one characteristic of a fluid circulating in a conduit in a flow direction, the autonomous device comprising:
    a rotor comprising a turbine capable of being driven in rotation by the fluid, the rotor being assembled to a stator, the turbine comprising a hub and a plurality of blades attached to the hub;
    an attachment feature allowing the stator to be fixedly placed in the conduit or at one end of the conduit, in a configuration in which an axis of rotation of the turbine is parallel to the flow direction;
    a permanent magnetic field source defining a magnetic plane perpendicular to the axis of rotation of the turbine;
    a magneto-electric converter having a reference plane and capable of transforming a variation in the reference plane of a magnetic field into a mechanical deformation capable of generating electric charges;
    a processing circuit, electrically connected to the magneto-electric converter, and configured to employ the electric charges to acquire a measurement of a characteristic of an environment in which the autonomous device is located; and
    a device for modifying the flow of fluid circulating in the conduit by modifying the passage cross-section of the conduit, the device comprising flaps or a curtain, opening of the flaps or the curtain providing a fluid circulation passage bypassing the blades of the turbine to limit the rotational speed of the rotor; and
    wherein one of the magneto-electric converter and the permanent magnetic field source is included in the stator, and the other one is included in the rotor, and the stator is connected to the rotor so that the reference plane of the magneto-electric converter resides in the magnetic plane generated by the permanent magnetic field source.

2. The autonomous device of claim 1, wherein the permanent magnetic field source is placed in the rotor and configured to rotate with the turbine, and wherein the magneto-electric converter is placed in the stator.

3. The autonomous device of claim 1, wherein the magneto-electric converter and the processing circuit are placed in the rotor, and wherein the permanent magnetic field source is placed in the stator.

4. The autonomous device of claim 2, wherein the magneto-electric converter and the processing circuit are in a sealed housing.

5. The autonomous device of claim 1, wherein an orientation of the blades is adjustable or the blades comprise a flexible material.

6. The autonomous device of claim 1, wherein the hub comprises a curtain capable of clearing a fluid circulation passage.

7. The autonomous device of claim 1, wherein the turbine is designed to have a speed parameter of less than three.

8. The autonomous device of claim 1, wherein the turbine has a strength between 0.7 and 1.

9. The autonomous device of claim 1, wherein a setting angle of the blades is between 15° and 45°.

10. The autonomous device of claim 9, wherein the setting angle of the blades is variable.

11. The autonomous device of claim 1, wherein the magneto-electric converter comprises, in its reference plane, a layer of magnetizable material, and is magnetically retained in the magnetic plane generated by the permanent magnetic field source so as to form a removable assembly between the rotor and the stator.

12. The autonomous device of claim 1, wherein the attachment feature comprise a conduit outlet, the rotor and the stator being placed inside the conduit outlet.

13. The autonomous device of claim 1, further comprising at least one sensor chosen from among a temperature sensor, a $CO_2$ or CO concentration sensor, a volatile organic particles sensor, a humidity sensor, or a turbine ID sensor.

14. The autonomous device of claim 1, wherein closing of the flaps or the curtain can be controlled to limit the passage area of the conduit.

* * * * *